United States Patent [19]

Rennolds

[11] 4,423,248

[45] Dec. 27, 1983

[54] PROCESS FOR ZONE REFINING WITH A HELICAL SOLUTION ZONE

[75] Inventor: Philip J. Rennolds, Wilmington, Del.

[73] Assignee: E. I. Du Pont de Nemours & Co., Wilmington, Del.

[21] Appl. No.: 327,059

[22] Filed: Dec. 3, 1981

[51] Int. Cl.$^3$ ............................................. C07C 45/79
[52] U.S. Cl. .................................... 568/324; 585/834
[58] Field of Search ......................... 568/324; 585/834

[56] References Cited

U.S. PATENT DOCUMENTS 3,449,087 6/1969 Saylor ................................... 23/296

OTHER PUBLICATIONS

Rabcyuk et al., Chem. Abst., vol. 95, #186921r (1981).
Rabcyuk et al., Chem. Abst., vol. 95, #186927x (1981).
McGhie et al., Amal. Chem., vol. 52, pp. 1738–1742 (1980).
Pfann, *Zone Melting*, Second Edition, John Wiley and Sons, New York, 1966, pp. 56 to 58 and 76 and 77.
Nicolau, J. Mater. Sci 5, 623 to 639.
Nicolau, J. Mater. Sci. 6, 1049 to 1060.

*Primary Examiner*—James H. Reamer
*Attorney, Agent, or Firm*—James A. Costello

[57] ABSTRACT

A process for refining an impure material using a helical solution zone and employing a common solvent for both material to be purified and impurity.

6 Claims, 1 Drawing Figure

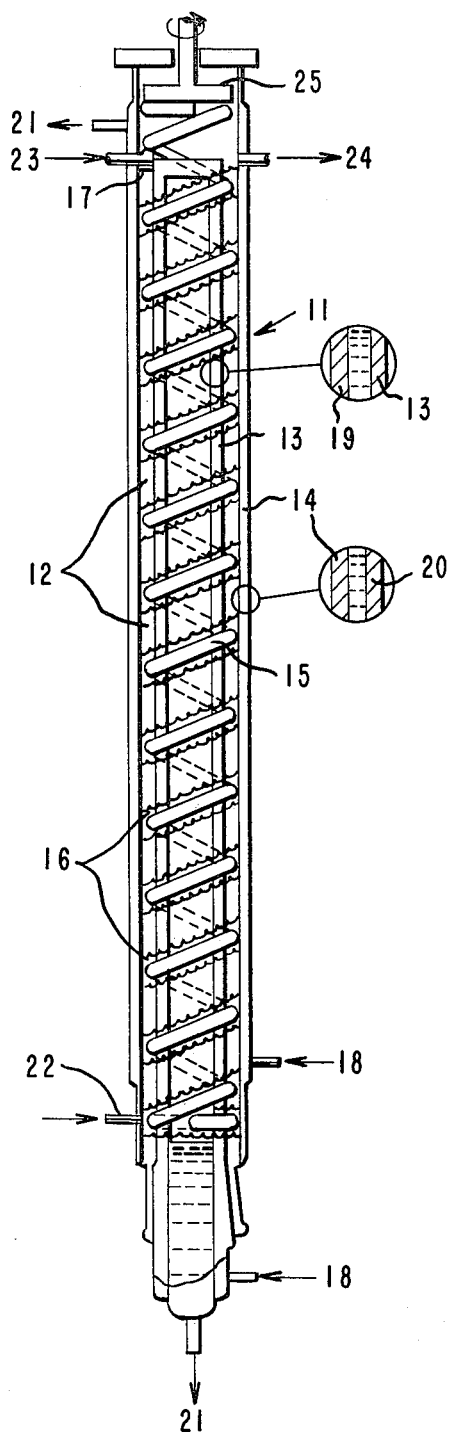

PROCESS FOR ZONE REFINING WITH A HELICAL SOLUTION ZONE

BACKGROUND OF THE INVENTION

This invention concerns a helical zone refining process employing a common solvent for the material to be purified and the impurity.

Zone melting of impure materials in helical zone refiners is known. See, for example, Pfann, *Zone Melting*, Second Edition, John Wiley and Sons, New York, 1966, pages 76 and 77. Use of a solvent in zone refining is known; see, for example, Pfann, ibid, at pages 56 to 58. See also, Nicolau, J. Mater. Sci. 5, 623 to 639 and J. Mater. Sci. 6, 1049 to 1060; and U.S. Pat. No. 3,449,087 (Saylor). However, no disclosure has been found concerning zone refining with a helical solution zone.

SUMMARY OF THE INVENTION

This invention concerns a method for refining a solid ingot of impure material contained in an annular sample space comprising:

(i) forming a continuous helical liquid solution zone from one end of the ingot to be purified to the other by heating the impure material at a temperature below its melting point along a helical path, said solution zone comprising solvent and the material to be purified, (ii) rotating the solution zone through the annular sample space thereby separating the pure material from the impurity, the method further characterized in that the pure material and the impurity are soluble in the solvent but to a different extent.

By "annular sample space" is meant a sample-containing region bounded by two surfaces such that the cross-section of the sample region, taken perpendicular to the container axis, is an annulus. It is convenient to use right circular cylinders for the sample containing surfaces. However, pairs of other surfaces can be used to give an annular sample region; for example, right circular cones, fractions of right circular cones, spheres, cylinders, and the like.

A helical liquid solution zone, wherein both the material to be purified and the impurity are dissolved in a common solvent, is in marked contrast to the makeup of the helical zone in a conventionally utilized helical zone refiner which comprises a melt of impure material in the helical path.

There are several advantages realized with the process of this invention heretofore unavailable in any single zone refining method:

(a) efficient separation of pure material from impurity employing a common solvent, (b) operation at temperatures below the melting point of the material to be refined, and (c) operation without displacement of the material being refined from one end of the zone refiner toward the other end.

For convenience herein, the primarily solid charge of material being refined may be referred to during its residency in the annular sample space as an ingot.

The method of this invention can be employed in both batch and continuous operation. In either form of operation, the solvent, which can be as small as 10% of the solid ingot volume or even smaller, can be recycled. In continuous operation, feed, product, and waste streams usually consist of solids dissolved in solvent and such streams require no handling of the solid ingot. In the method of this invention, the crystallization rate should be high enough to allow a practical rate of zoning. Furthermore, the material to be purified, impurities and solvent should not react with the material of which the refiner is made.

Purification at the relatively low temperatures employed in the method of this invention enables the zone-refining of materials not amenable to a refining process which relies on melting the impure material. Such materials include those which decompose on melting, have too high a melting point, have too high a vapor pressure at the melting point, are too reactive in the melt condition, or form a glassy structure when cooled from the melt.

The temperature coefficient of solubility of the material to be purified in the solvent should be positive, i.e., increase with temperature, but the solvent itself must not be soluble in the crystalline pure material. The material to be purified should form a compact crystal mass to minimize solvent entrapment.

BRIEF DESCRIPTION OF THE DRAWING

The FIGURE depicts, in cross-section, a helical solvent zone refiner that can be employed in the process of this invention.

DETAILS OF THE INVENTION

There are many materials which can be purified by the process of this invention. For example, anthracene can be purified from a mixture with methylanthracene employing tetrahydrofuran as solvent. Benzil can be purified employing ethanol as solvent.

APPARATUS

The preferred apparatus for practicing the method of this invention is one in which the annular sample-container remains stationary with the helical heater rotating through the annular sample space. Alternately, the heater can be external to the sample-container and either heater or sample-container rotated while the other remains stationary.

This invention can be more fully understood with relation to the apparatus, 11, of the FIGURE in which the helical heater rotates through a fixed sample-containing zone. The material to be refined is contained in the annular region, 12, between two concentric jacketed cylinders. That is, the charge of normally solid material is contained between the outer wall, 13, of the inner cylinder and the inner wall, 14, of the outer cylinder. A helical heater, 15, contains hot fluid or, alternatively, is heated by electrical (Joule) heating or radiofrequency heating. Helical heater, 15, is surrounded by a helical-shaped solution zone, 16, in which the material to be purified is in liquid solution in an otherwise solid charge of material, the top of which is at 17.

Coolant enters the refiner through inlets, 18, flows through the inner and outer cylindrical jackets, between walls 13 and 19 to cool the inner sample-containing wall, 13, and between walls 14 and 20 to cool the outer sample-containing wall, 14. The coolant exits at outlets, 21. Inlet, 22, is provided for charging the material to be purified and the solvent into annular region, 12. In a preferred embodiment of the method of this invention, as solvent reaches the top of the helical zone, it is entrained in a stream of inert gas, e.g., nitrogen or the like, introduced via inlet, 23, and exiting outlet, 24. Outlet, 24, leads to a refrigerated trap (not shown). Alternatively, the solvent can be vaporized by a heater (not shown) and exit 24 in the vapor state leaving its solute (rich in pure material or impurity) in the refiner, to be removed in solid form. The heater, 15, affixed to rotating disc, 25, is rotated slowly, the corresponding solution zone rotating with it. For the direction of motion shown by the arrow, the heating motion is downward to move the crystallizing interface downward.

Typical materials of construction useful to fabricate a refiner such as that depicted in the FIGURE include glass and steel. Complementary materials of construction can be employed as heater elements, tubing, gaskets, end closures, etc. Solvent can be let in via tubing of any material, e.g., polytetrafluoroethylene, which will not be adversely affected by the solvent. Typical dimensions of the outer cylinder having inside wall 14 and the inner cylinder having outside wall 13 are 57 mm OD and 35 mm OD, respectively. Typical length of sample space is about 25 cm and width, 8 mm.

The heater, 15, can be formed by inserting a length of Nichrome wire into a sheath of polytetrafluoroethylene, then doubling the wire in its sheath, so that its free ends are together and inserting this bifilar resistance element into a straight length of metal tubing. The metal tube is sealed at its lower and, then wound on a rigid mandrel to provide a helix. The lower and upper ends of the helix are provided with a single "flat" turn of the tube perpendicular to the axis of the helix. The upper end of the helix is terminated by a straight length of tubing carefully aligned on the central axis of the helix. The straight length of tubing is passed through the sealing gland in standard-taper joint. The resistance wires may be connected to a set of electrical commutator rings. A gear or sprocket is attached to the straight length of tubing, for connection to a source of rotary power to rotate the heater. The heater is inserted between tubes 13 and 14 of the FIGURE and the cap and container tube are secured by a clamp. Rotation of the heater is functionally equivalent to conventional zone transport along the axis of the annulus. Heat is transferred simply and effectively from the solid/liquid interface to adjacent inner and outer cooling jackets. It should be noted that the helical heater can have a circular, elliptical, or other cross-section. Further, the heater need not contain electrical resistance wires. Instead, the helical metal element can be energized by an exterior coil which provides radiofrequency radiation. In this case, the helical heater can also serve as a conduit for the introduction of fluid into the sample space, as described later in connection with continuous operation.

The helical heater width must be small enough so that the helical heater rotates easily within the annular sample space but sufficiently large so that the liquid solution zone extends across the width of the sample-containing space from one containing wall to the other, at ordinary rates of zoning which will be up to about 24 revolutions per day. The pitch of the helix must be chosen so that there is sufficient solid material between adjacent turns of the helix to provide enough heat conduction to allow crystallization of the sample at the trailing edge of the helical solution zone. For ease of operation, the ratio of the height of the annular sample space to the diameter of the annular sample space should be small. However, some minimum height is required to prevent diffusive mixing of pure and impure material. Generally, this ratio should be between about 3 to 10.

In batch operation, inlet 22 is connected to a pump which in turn is connected to a reservoir of solvent. The sample of material to be purified is melted and poured into the annular sample space between tubes 13 and 14. Another possibility is that the sample can be introduced under hydrostatic pressure through inlet 22 along with the solvent. Electrical power is provided to the resistance element within the helical metal coil and the voltage is adjusted by suitable means such as an autotransformer, to produce a thin layer of melt on the surface of the helical heater.

Solvent is introduced either by gravity from an elevated source, or by means of a pump (not shown). The solvent displaces a part of the melt from the surface of the helical heater. It is desirable that the sample material have a large, positive temperature coefficient of solubility in the solvent that is selected. The temperature of the heater is adjusted so that it is several degrees or more below the boiling point of the solvent, and the temperature of the heat-exchange fluid inside and outside the annular sample space is adjusted so that it is about 10 degrees cooler than the heater. Under these conditions, rotation of the heater causes dissolution of the sample in the solution zone at the leading edge of the heater, and crystallization of the sample from the solvent at the trailing edge of the heater.

It is preferred to maintain a flow of solvent into the solution zone. The solvent flow rate is adjusted so that the liquid zone contains a steady concentration of solvent adequate for formation of a monolithic deposit of crystals from solution. The flow rate must not be so great that the solution zone is depleted of material to be purified. As solvent reaches the top of the helical zone, it can be entrained in the stream of inert gas introduced via inlet 23 and carried through outlet 24 to a refrigerated trap. The recovered solvent is returned to the solvent reservoir, either periodically or continuously. This mode of operation results in a redistribution of impurities in the solid ingot, removed from one end and concentrated in the opposite end.

In continuous operation, feed stream(s) of solvent and material to be purified are added continuously and pure material, impurity, and solvent are removed continuously, with the solvent optionally recycled. In continuous operation, external heaters and connections are usually added at each end of the refiner and at the entry point(s) of the feed stream(s) to provide annular liquid solution zones in continuous contact with the helical solution zone. The entry point for the material to be purified (and the solvent) is preferably located between the two ends of the refiner where the steady state solute profile has the same concentration as the material to be purified.

The following Examples illustrate the invention.

EXAMPLE 1

A 250 g batch of benzil containing a small amount of impurity was melted and charged into the annular sample space of a refiner like that depicted in the FIGURE, with the exception that the heater had only 5 turns. The internal helical heater was energized and the solvent ethanol was passed through the helical zone at the rate of 3 ml/hr. After 5 revolutions of the helical heater at a rate of one revolution per day, heating was discontinued and the ethanol drained from the helical zone. In this instance, because the impurities were less soluble in the ethanol solvent than was the benzil, the impurities were concentrated in the lowermost zone during the upward zoning.

The ingot was collected in four fractions as follows. A heater was used to melt four fractions of the zoned ingot. Each melted fraction was aspirated into a receiver from which a sample was removed for analysis by mass spectrometry along with a sample of the starting material. The results are shown in Table 1.

TABLE 1

| Fraction | Area in Major Peak Percent | Impurities, Percent |
| --- | --- | --- |
| Starting Material | 99.86 | .14 |
| 1 (bottom) | 99.77 | .23 |
| 2 | 99.94 | .06 |
| 3 | 99.92 | .08 |
| 4 | 99.95 | .05 |

After 5 passes of the helical solvent zone, the ingot showed a gradient of impurity concentration from a value at the bottom of the ingot which is 1.6 times that of the starting material to a value at the top of the ingot which is 0.36 that of the starting material. This result confirms the efficacy of the rotating solution zone to redistribute impurity.

EXAMPLE 2

A 26.6 g batch of anthracene containing the impurity, methylanthracene, was melted and charged into the annular sample space of a helical zone refiner constructed generally as depicted in the Figure. In this instance, however, the heater was mounted outside the sample-containing zone and the heater had 5 turns. The heater utilized a Nichrome resistance element wound helically with rubber tubing of semi-circular cross-section provided between the turns of the heater for circulation of coolant. The heater/cooler was clamped around the vessel which rotated about its axis within the fixed heater/cooler.

The heater was energized and the solvent, tetrahydrofuran (THF), was passed through the helical zone at the rate of 2.6 ml/hr while the zone was revolving at a rate of 6 revolutions per day. The total amount of THF used (104 ml) was less than would have been required to dissolve the 26.6 g batch even one time since the solubility of anthracene in THF is only 7 gm/100 ml at the boiling point. The THF was recycled.

After 10 revolutions, heating was discontinued and the THF was drained from the sample space. Four fractions of the zoned ingot were collected as described in Example 1. The concentration, C, of the methylanthracene in each of the four fractions, relative to the concentration, $C_o$, in the starting material, is shown in Table 2.

TABLE 2

| Fraction | Relative Concentration, $C/C_o$ |
| --- | --- |
| Starting Material | 1.00 |
| 1 (top) | 4.04 |
| 2 | 3.71 |
| 3 | 0.69 |
| 4 | 0.50 |

The methylanthracene impurity was more soluble in the THF than was the anthracene and therefore was concentrated in the uppermost region during the upward zoning. It can be seen from Table 2 that the moving solution zone produced a gradient of impurity concentration from 4 times higher to ½ that of the starting material.

I claim:

1. A method for refining a solid ingot of impure material contained in the annular sample space of zone refiner comprising:
   (i) forming a continuous helical liquid solution zone from one end of the ingot to be purified to the other by heating the impure material at a temperature below its melting point along a helical path, said solution zone comprising solvent and the material to be purified,
   (ii) rotating the solution zone through the annular sample space thereby separating the pure material from the impurity, the method further characterized in that (a) the pure material and the impurity are soluble in the solvent but to a different extend and (b) there is no displacement of the ingot from one end of the zone refiner to the other end.

2. A method according to claim 1, comprising continuously adding impure material and solvent and continuously removing pure material, impurity and solvent.

3. A method according to claim 2, comprising recycling the solvent.

4. A method according to claim 3, comprising rotating a helical heater through the annular sample space.

5. A method according to any one of claims 1 to 4 wherein the impure material is benzil and the solvent is ethanol.

6. A method according to any one of claims 1 to 4 wherein the impure material is anthracene, the impurity is methylanthracene, and the solvent is tetrahydrofuran.

* * * * *